US012758112B2

(12) United States Patent
Saliga

(10) Patent No.: US 12,758,112 B2
(45) Date of Patent: Oct. 13, 2026

(54) METHOD FOR MEASURING THE IMPEDANCE OF A BIOLOGICAL LOAD USING LOW POWER DIRECT CURRENT

(71) Applicant: MB DEVICE LLC, Louisville, KY (US)

(72) Inventor: Thomas V. Saliga, Tampa, FL (US)

(73) Assignee: Occam Design, LLC, Louisville, KY (US)

( * ) Notice: Subject to any disclaimer, the term of this patent is extended or adjusted under 35 U.S.C. 154(b) by 857 days.

(21) Appl. No.: 17/851,575

(22) Filed: Jun. 28, 2022

(65) Prior Publication Data

US 2022/0330846 A1 Oct. 20, 2022

Related U.S. Application Data

(60) Continuation-in-part of application No. 17/516,805, filed on Nov. 2, 2021, now abandoned, which is a division of application No. 16/285,714, filed on Feb. 26, 2019, now abandoned.

(51) Int. Cl.

| | |
|---|---|
| ***A61B 5/053*** | (2021.01) |
| ***G01N 27/02*** | (2006.01) |
| ***G01N 33/483*** | (2006.01) |
| *G11C 27/02* | (2006.01) |

(52) U.S. Cl.

CPC ........... *A61B 5/053* (2013.01); *G01N 27/026* (2013.01); *G01N 33/4833* (2013.01); *G11C 27/02* (2013.01)

(58) Field of Classification Search

None

See application file for complete search history.

(56) References Cited

U.S. PATENT DOCUMENTS

| | | | | |
|---|---|---|---|---|
| 4,743,855 | A | 5/1988 | Randin et al. | |
| 5,047,722 | A | 9/1991 | Wurst et al. | |
| 5,585,728 | A | 12/1996 | Champlin | |
| 5,606,242 | A | 2/1997 | Hull et al. | |
| 5,633,573 | A | 5/1997 | van Phuoc et al. | |
| 5,650,937 | A | 7/1997 | Bounagn | |
| 5,773,978 | A | 6/1998 | Becker | |
| 5,917,479 | A | 6/1999 | Haapakoski | |
| 6,002,238 | A | 12/1999 | Champlin | |
| 6,714,814 | B2 | 3/2004 | Yamada et al. | |
| 6,820,019 | B1 | 11/2004 | Kelly et al. | |
| 7,391,257 | B1 | 6/2008 | Denison et al. | |
| 9,682,234 | B2 | 6/2017 | Hogg et al. | |
| 10,154,922 | B1 * | 12/2018 | Perez | A61N 1/0502 |
| 2001/0051774 | A1 * | 12/2001 | Littrup | A61B 5/4312 600/547 |
| 2007/0106342 | A1 * | 5/2007 | Schumann | A61H 39/002 607/46 |
| 2007/0114971 | A1 | 5/2007 | Uesaka et al. | |
| 2007/0293910 | A1 | 12/2007 | Strother et al. | |
| 2010/0268495 | A1 | 10/2010 | Armstrong et al. | |
| 2011/0313311 | A1 * | 12/2011 | Gaw | A61B 5/4331 600/547 |
| 2019/0021647 | A1 * | 1/2019 | Zheng | A61B 5/7225 |
| 2019/0192064 | A1 * | 6/2019 | Cantor | A61B 5/746 |

* cited by examiner

*Primary Examiner* — Aurelie H Tu

(74) *Attorney, Agent, or Firm* — John E. Vanderburgh

(57) ABSTRACT

A method for simulating alternating current from low power direct current and determining tissue impedance of a biological load.

9 Claims, 9 Drawing Sheets

METHOD FOR MEASURING THE IMPEDANCE OF A BIOLOGICAL LOAD USING LOW POWER DIRECT CURRENT

REFERENCE TO RELATED APPLICATIONS

This application is a continuation-in-part of application Ser. No. 17/516,805, filed Nov. 2, 2021 which is a divisional application of application Ser. No. 16/285,714, filed Feb. 26, 2019.

BACKGROUND OF THE INVENTION

There is a need for Electrical Impedance Spectroscopy (EIS) in a variety of industries. For example, this technique is used to measure two-terminal impedance over a wide frequency range in material and biomedical sciences. With measurement frequencies less than about 100 KHz, the EIS technique often uses a Kelvin type connection to the target material. The Kelvin method normally drives a constant and known sinusoidal current of specified frequency into the target material using one pair of electrodes and then, with a second pair of interposed electrodes, measures the real and imaginary voltage components using multiplicative phase detectors, amplifiers and data acquisition methods. The ratio of these "real" and "imaginary" voltages to the known drive current is the impedance at the drive frequency. The physical equipment to implement EIS is normally quite large as compared to, say, a postage stamp. Further, this equipment requires multiple watts of power during operation. However, new applications for EIS require substantial miniaturization and extremely low power compatible with long term, unattended battery operation.

For example, the medical arena of wearable medical monitors is now becoming popular and, in particular, Electrical Impedance Tomography holds promise for identifying various medical disorders before they are otherwise apparent. (ref. 1, 2). This application requires that a plurality of EIS devices be placed on a patient's body and that ideally, the person must be ambulatory and able to function normally. Further, EIS is shown to be particularly helpful in the prediction of premature births (ref 3, 4, 5). These applications require a substantially smaller measurement device which operates with micro-watts of average power. No such device is known to be available.

What is sought is an EIS means and method which is capable of measuring biological impedances from 10 Hz to 100 KHz, is capable of being miniaturized to approximately one-half the size of a postage stamp with a thickness of tens of mils and able to function on similarly small batteries for days to months. Further, it's collected EIS data must be wirelessly accessed on a regular interval to fulfill its "wearable" mission. The subject invention employs very small micro-computer-based techniques with a minimal number of external components to accomplish the above goals and is hereafter called the Pulsed-Kelvin Impedance Measurement method (PKIM).

SUMMARY OF THE INVENTION

The system and the method of this invention is herein referred to as Pulsed Kelvin-connected Impedance Measurement (PKIM). PKIM can be employed wherever miniaturization and low power usage are required to determine potential of current flow through a biological load such as, for example, measuring impedance of biological tissue.

In accordance with the invention, a series of timed, voltage pulses at a first polarity of known frequency, amplitude and driver resistance followed by a series of timed, voltage pulses at an opposite polarity of known frequency, amplitude and driver resistance are applied to a material, typically a biological load, via at least two separate electrodes operatively connected to specifically timed sample and hold circuits. The voltage output from these sample and hold circuits is converted to numbers with one or more analog-to-digital convertors (ADC). By a combination of local data processing and post-processing of these numbers, the desired EIS data is extracted and reported.

DETAILED DESCRIPTION OF THE INVENTION

As used hereinafter the term "biological load" refers to biological tissue for which determination of tissue impedance is desired.

As used herein the term "sample" means a rapid closure, then opening of a switch which is coupled to a time varying voltage source. The switch closure time is understood to be small compared to the time rate of change of the voltage source. This switch is coupled to an ADC or a capacitor for charge-up purposes.

"Sampling" may be considered to be the act of sensing a potential at a specific point in time on a time varying potential source, and this potential source may have a non-zero source impedance.

"Binary" as applied to current pulses means that the pulse may be positive or negative depending on the polarity of the circuit.

Figure 1:
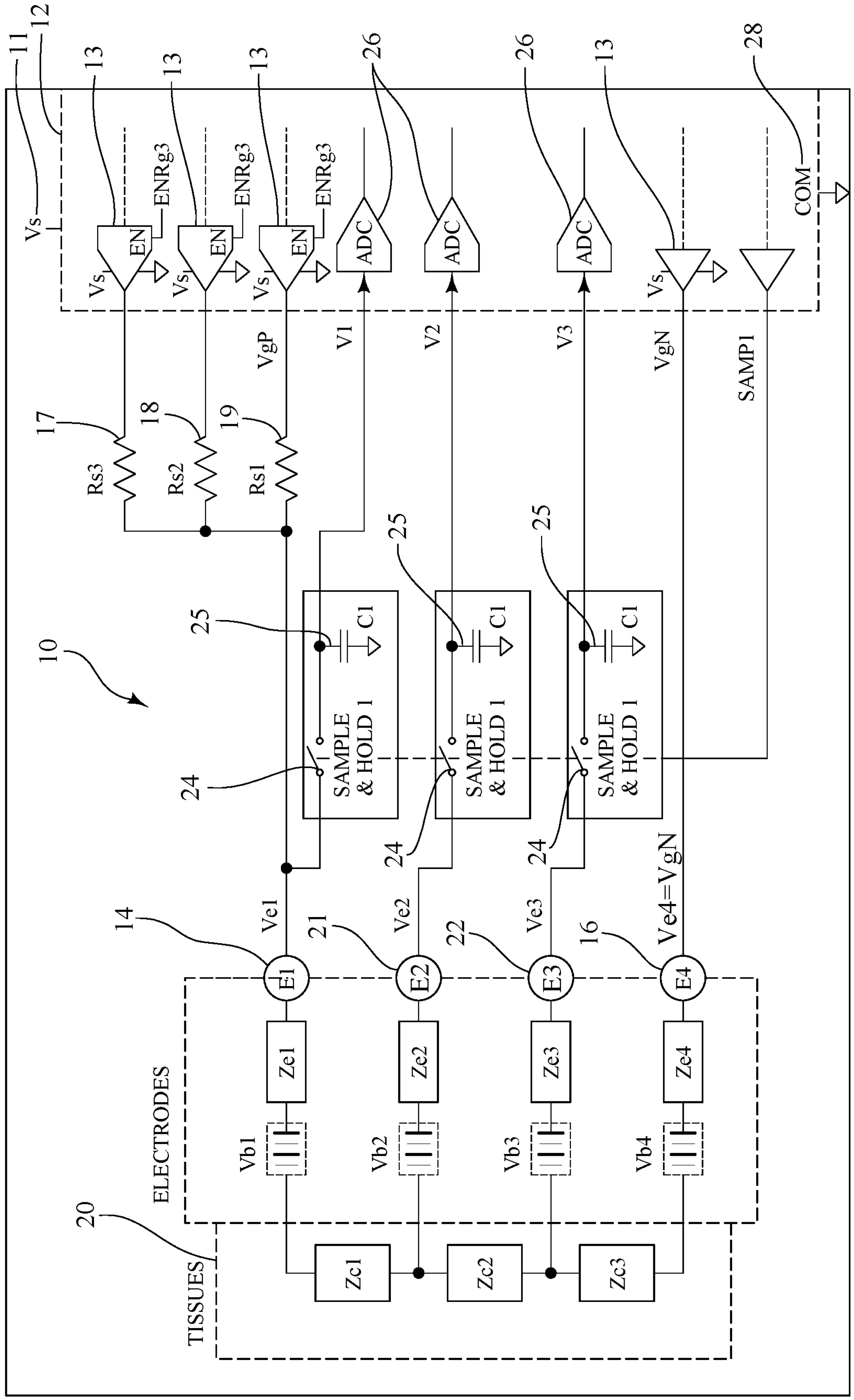
FIG. 1 is a schematic representation illustrating the basic elements of a low parts-count and low power circuit connected to an electrical model of the electrodes and tissue in accordance with the present invention.

Referring to FIG. 1, the essential hardware elements of the PKIM micro-device 10 are shown along with an electrical model of the electrodes and connected tissues. A primary goal is the measurement of tissue impedance, Zc2, over a range of frequencies as if the binary excitation potentials (VgP and VgN) were pure sinusoidal waves.

In an embodiment of the invention, a low power direct current source 11 provides positive supply voltage (Vs) to a micro-controller 12. Micro-controller 12 drives a series of current-limited positive voltage pulses through resistors 17, 18 and 19 into a biological load via the positive injection electrode 14 followed by reversing the polarity of the supply voltage and driving a series of current-limited negative voltage pulses into the biological load via the negative injection electrode 16.

The current is limited by the resistors 17 (1.0K), 18 (3.16K) and 19 (10K) which may be enabled by the micro-controller 12 in any combination. These resistors set a desired range of current injected into the tissues via electrodes 14 and 16. It is understood by one skilled in the art that additional resistors and micro-controller port drivers could be employed if so desired. The actual current driven into the tissues may be computed by measurement of the potential at electrode 14 (Ve1) and a knowledge of the pulse drive voltage, (VgP) for positive pulses and at electrode 16 and a knowledge of pulse drive voltage (VgN) for negative pulses. VgP and VgN are typically the micro-computer's supply voltage for positive pulse production or supply voltage through the local common 28 for negative pulse production.

The Kelvin-configured electrodes 21 and 22, are coupled to fast analog switches 24 which in turn connect to relatively large storage sample and hold capacitors 25, (C1), to accumulate charge from specifically timed samples of the tissue potentials. The sample and hold capacitors 25 permit conventional, slower sampling analog to digital converters 26 (ADC's) to be used without incorporating active operational amplifier buffers at the electrode nodes 14, 16, 20 and 22. This reduces parts count and power draw, both critical to the intended applications.

As illustrated, the polarity of the circuit is positive, and the resulting pulses are positive. Reversing current flow by drawing the supply voltage through the local common 28 reverses polarity of the circuit and the resulting pulses are negative. Circuit polarity is controlled by the micro-controller 12.

By application of PKIM, applicant can:

a. substantially reduces the parts count and size of the circuitry as compared to conventional AC coupled, sinewave driven, dual-phase detector EIS;
b. measure real and imaginary impedance components of any impedance in a frequency range under approximately 100 KHz provided the impedance does not rise sharply with frequency.
c. in the special case of human tissue impedance, extract the real-component of a low frequency (25 Hz), mid-frequency (2 KHz) and high frequency (100 KHz) equivalent cervical tissue impedance, Re [Zc2], with good accuracy. For example, these particular impedances are an early measure of the physiological condition of tissue.
d. measure the total electrode to electrode impedance (14 to 16) over a similar binary range of frequencies. For the special case of breast tissue impedance monitoring, this may be a more reliable indicator of cancer in a continuously monitored patient; and produces a circuit that operates on low power and can be fitted into a small sensing device.

The system of the present invention includes circuitry that is miniaturized and operates on a low voltage DC supply such as a 3 volt battery. Present day micro-controllers such as the Texas Instruments MSP430 series have become quite competent with peripheral resources and the invention's methods attempt to take advantage of those capabilities to reduce parts count and size of the PKIM process.

Conventionally, an EIS measurement system employs sinusoidal voltage drive signals of alternating current to the measured tissues. The potential through the biological load is used to determine the impedance of the biological load. However, the use of alternating current requires circuitry employing large capacitors and more components which render miniaturization of the circuit.

In accordance with the invention the two embodiments are described to approximate alternating current for EIS determinations using a binary pulse driver. The first embodiment modifies the pulse timing to better approximate the harmonic content of a sine wave.

Figures 2A, 2B, 2C:
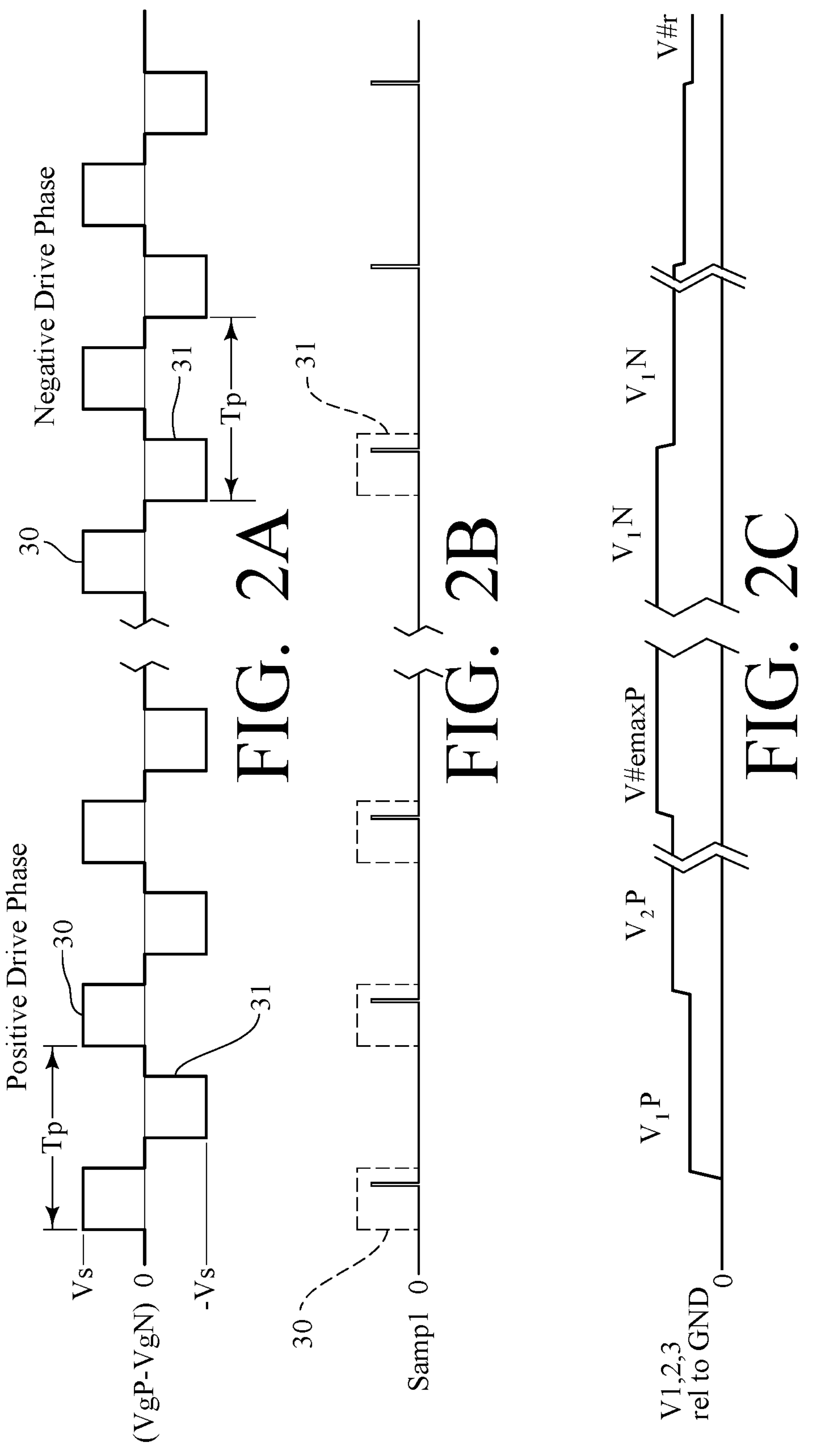
FIG. 2A illustrates potential input to a biological load showing positive and negative input pulses of selected frequency.
FIG. 2B illustrates preferred pulse sampling points.
FIG. 2C illustrates a simplified diagram illustrating potential increase from each pulse sampling at output of the sample and hold devices.

For example, in an embodiment instead of complex sinewave shaping of the voltage drive to the Kelvin electrodes, micro-controller 12 port-driven, square wave positive pulses (VgP) 30 and square wave negative pulses (VgN) 31 are used as shown in FIG. 2A. These pulses alternate between the known power supply battery voltage and local common 22. For purposes of illustration only three positive and three negative pulses 24 are shown in FIG. 2A. However, it will be understood that the number of pulses, the duration of each pulse, the time of sampling and the number of samples taken is largely dependent on the frequency of the pulses. The microcontroller 12 is programed to select the sampling time and the number of pulses in a series of pulses applied across the biological load. One pulse time cycle is shown as Tp.

By proper pulse timing, the odd harmonic components of these pulses are substantially reduced, permitting a much closer approximation to a sinusoidal drive waveform. As illustrated in FIG. 2B sample points are chosen at the approximate 135° cycle point so that both the real and reactive components of Zc2 are measured.

FIG. 2C shows the increase in the charge at a capacitor 25 as subsequent pulses are sampled. As illustrated, maximum potential is achieved after only increments of three pulses are sampled, however, normally a larger number of pulses must be sampled to achieve maximum potential. The number of pulses sampled is not critical so long as an enough are sampled to reach maximum potential for the biological load being measured for its impedance. Sampling after maximum potential has been reached has no further effect on the charge of the capacitor 25.

Figure 4A:
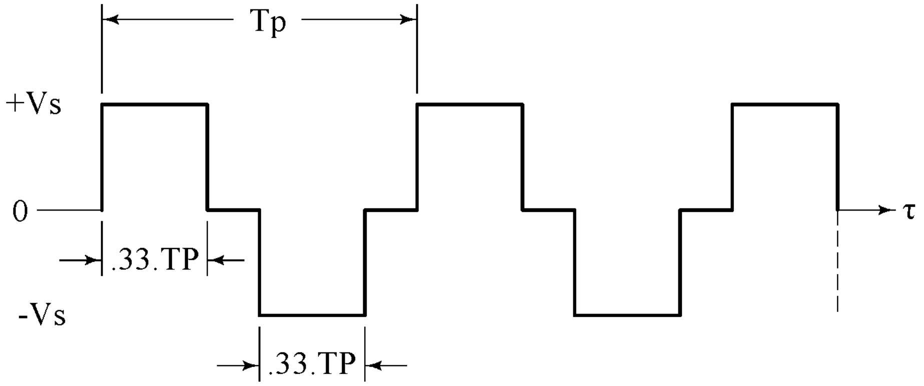
FIG. 4A is representative of the pulse potential waveform applied across electrodes connected to the tissue to be measured.
Figure 4B:
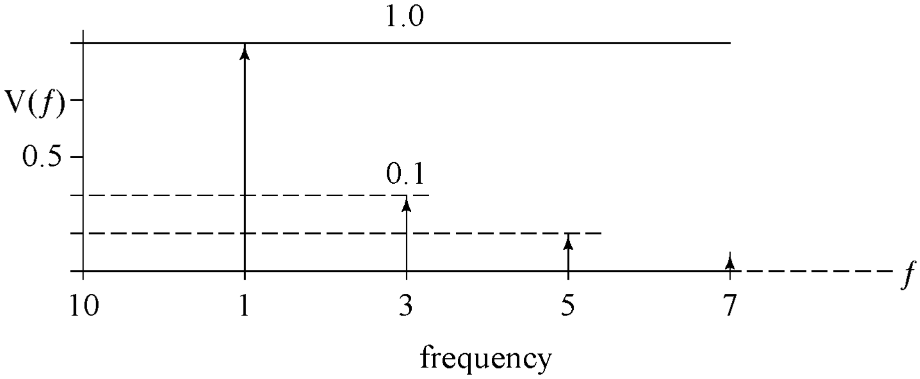
FIG. 4B plots the relative voltage versus of the pulse waveform shown in FIG. 4A.

FIG. 4A illustrates a method in which a square waveform is modified such that the timing of the non-zero potential of a pulse during any ½ cycle is approximately 66% of the total period. With this condition, the third harmonic is reduced from $1/3^{rd}$, as it would be for a square wave, to approximately one tenth. The higher odd harmonics are also reduced.

Figure 3A:
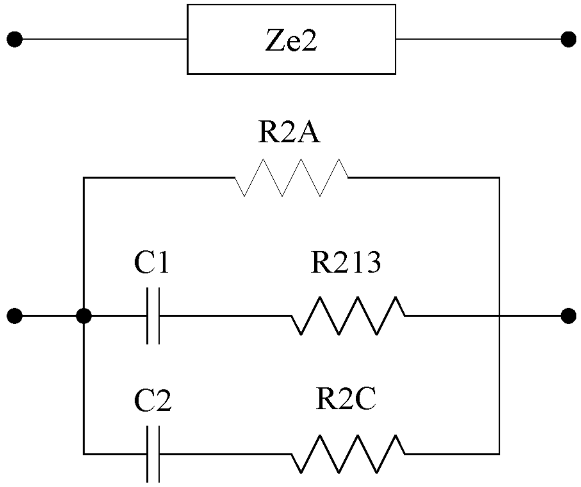
FIG. 3A is an electrical schematic of the approximate equivalent circuit of internal human tissue, where Ze2 represents tissue impedance, and is representative of the circuit resistances to be measured.
Figure 3B:
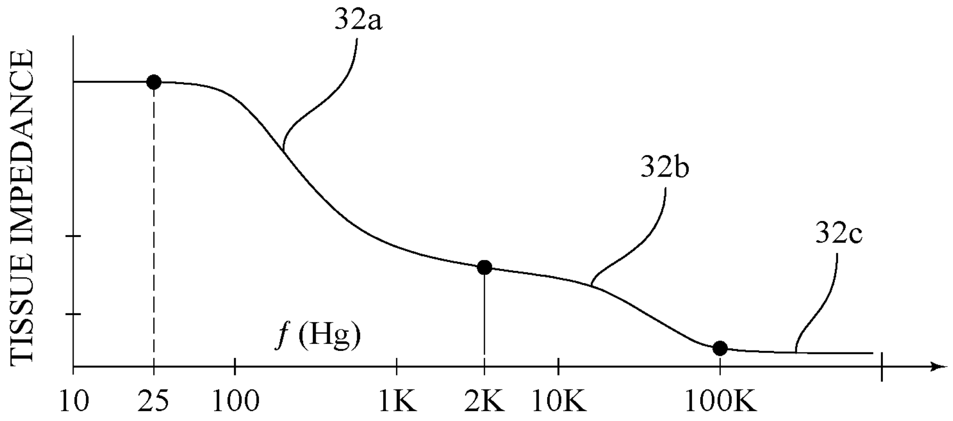
FIG. 3B is a plot representative of the magnitude of tissue impedance versus frequency

A second embodiment used to approximate a sinusoidal driven EIS system is to select drive frequencies in which the pulse harmonics encounter essentially the same impedance as the fundamental frequency. FIG. 3B is a sketch of typical tissue impedance versus frequency. Note that there are three plateaus, 32*a*, 32*b* and 32*c*. By choosing a fundamental frequency at the lowest frequency in each plateau, the pulse's higher harmonics encounter essentially the same resistive value as the fundamental frequency. As illustrated the selection points are located at 25 Hz, 2 KHz and 100 KHz as convenient frequencies. However, other fundamental frequencies can be selected along the plateaus with good results. Thus, by incorporation of the above two methods, the measured EIS impedance closely approximates an ideal sinusoidal based EIS system.

Some versions of the micro-controller 12 include up to four Delta-Sigma, 24 bit Analog-to-Digital convertors (ADC) permitting extra-ordinarily small signals to be digitized with adequate resolution for these EIS applications. However, the Delta-Sigma ADC's acquisition time is too long to acquire phase-sensitive analog data for frequencies much higher than 5 KHz. Further, while available microcontroller ADCs incorporate their own sample and hold circuits, these circuits require a low-impedance drive source and are not suitable therefore to be directly connected to biological tissues. PKIM employs a novel repetitive sampling method to affect the desired measurement while using this type of ADC. FIG. 5 details this method.

Figures 5A, 5B, 5C:
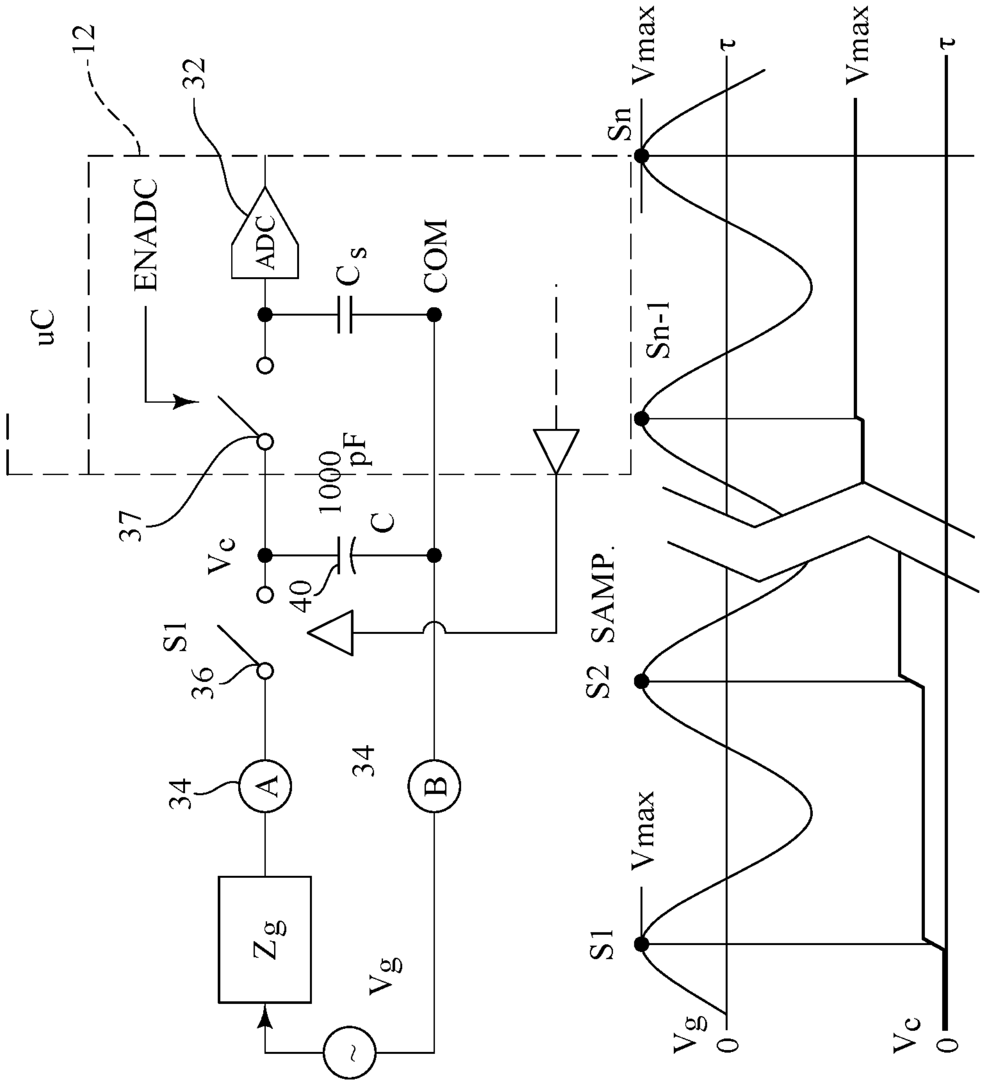
FIGS. 5A, 5B and 5C detail how a repetitive sampling of a high impedance voltage source is used to charge a suitably large capacitor to enable a slow, low input impedance ADC to be employed in the PKIM measurement process.

Referring to FIG. 5A a simplified circuit diagram illustrates the principal of PKIM operation. A voltage-generator 34 (Vg) with series impedance, Zg simulates a voltage as might be measured by electrodes connected to tissues. Series impedance, Zg, may have a value in the 5,000-ohm range. PKIM sampling switch 36 rapidly closes and then opens at a desired sample point S1 on the Vg waveform as shown in FIG. 5B. Microcontroller 12 controls switch 36 through line 38. The switch closure period may be in the one to two microsecond range. When the switch is closed, the voltage Vg charges sample and hold capacitor 40, via the series impedance, Zg. The sample and hold capacitor 40 may have a value of approximately 1000 pF. During the short closure time of switch 36, sample and hold capacitor 40 can only charge up partially. It is well known that the Zg x capacitor time constant would be about 16 micro-seconds. Thus, a single sample period of two microseconds would not allow the voltage Vc to equal the actual desired voltage, V max as shown in FIG. 5B. However, by repeatedly sampling at the same point on the Vg waveform, the sample and hold capacitor 40 will accumulate charge in packets and, with enough samples, the voltage Vc will rise to closely equal V max. Once V max is reached additional sampling adds nothing the charge of the sample and hold capacitor 40. FIG. 5C illustrates how the voltage across the sample and hold capacitor 40 rises with enough repeated sample cycles to eventually equal the desired sample value. Once the sample and hold capacitor 40 has this final value, no more current is drawn from the tissue source generator and enough energy is stored in the sample and hold capacitor to close switch 37 and complete the circuit to an ADC 32 of a conventional microcontroller 12 so that it can make its conversion with little error. By this means, PKIM eliminates the need for analog buffer amplifiers with a consequent reduction in parts count, size and power draw.

Further. in conventional EIS instrumentation, relatively large AC coupling capacitors are typically used with biological tissue measurements because the electrode to tissue conductors form a half-cell potential which can severely bias the computed impedance results. This equivalent DC voltage is shown in FIG. 1 as potentials Vb1, Vb2, Vb3 and Vb4. Further, these coupling capacitors increase data acquisition time since they may have a significant RC time-constant settling time after a frequency or polarity change.

However, the PKIM method employs a novel method to eliminate this requirement which further reduces size, parts count and, due to a lower data acquisition time, it also reduces average power draw. Electrodes connected to tissues typically develop half-cell potentials as shown in FIG. 1. Each electrode's dc bias voltage, Vb1, Vb2, Vb3 Vb4, may develop DC potentials of 0.2 vdc or more. Unless accounted for or cancelled out, these will cause substantial errors in measurement of the tissue impedance. As noted earlier, typical EIS instruments employ AC coupling capacitors. To forestall their use and keep component count and size to a minimum, PKIM takes advantage of the microcontroller 12 binary port drivers 13 to invert the drive potentials at Ve1 and Ve4 and make a second series of sampled measurements at each frequency so that DC offsets are cancelled. For example, and with reference to FIG. 1 and FIG. 2, as illustrated a first set of sampled measurements (resulting in V1, V2, V3 ADC values) are made with electrode 16 held at common or ground potential so that positive pulses VgP are injected into the biological load 20. Then a second set of sampled measurements are made with electrode 14 held at common while negative pulses VgN are injected into the biological load 20. By averaging a "positively driven" impedance and a "negatively driven" impedance, and taking their average, an unbiased impedance value may be derived.

It is important to note that, in practice with biological loads, the electrode DC offsets (Vb #) will change when driven with an AC signal versus direct measurement. Thus, simply measuring Vb # by making VgP and VgN zero and then subtracting that value from AC measured sample values will not usually give a correct result. For instance, in one case, a zero excitation DC potential between two electrodes connected to a biological load measured 55 millivolts but when excited by AC currents, it increased to 83 millivolts. With a 3V supply voltage-based measurement, this difference would cause substantial measurement error if a direct DCV offset correction method had been used.

In a conventional EIS system using Kelvin configured electrodes, a constant-current, sinusoidal signal is applied to the E1 and E4 electrodes. However, due to the low battery voltage (3V approx.) and minimal parts count goal, a constant-current driver is not a good choice. Further, as will be described, the above DC offset correction method requires that the measured voltage drop across the Kelvin electrodes (E2, E3) not reverse in potential sign due to comparatively large bias voltages, Vb2, Vb3. This places a lower limit on the current and hence the voltage drop across the biological load. Therefore, the pulse generator's current sensing resistor, Rg, must not be too large relative to the biological load impedance at the frequency being tested.

There is yet another important PKIM design consideration in the selection of Rg at the frequency being tested. Specifically, the selected Rg and the magnitude of the pulse amplitude potential (i.e.: the supply voltage, Vs) should not cause the total voltage across electrodes E1 and E4 to exceed approximately 2.1 volts or else electrolysis may take place at those electrode sites.

Thus, the choice of resistance, Rg, for proper PKIM operation on biological loads must be "windowed" between some minimum and some maximum value at each frequency measured before the actual measurement is made. A PKIM process for accomplishing this selection automatically is detailed in the flow diagram of FIG. 6. The goal of this Rg selection method is to select a generator driver resistance which assures that the tissue measurement voltages are large enough to overcome the accumulated DC bias offset voltages of the electrodes but not so large as to cause electrolysis to occur. It is assumed that a plurality of Rg selections is implemented.

Figure 6:
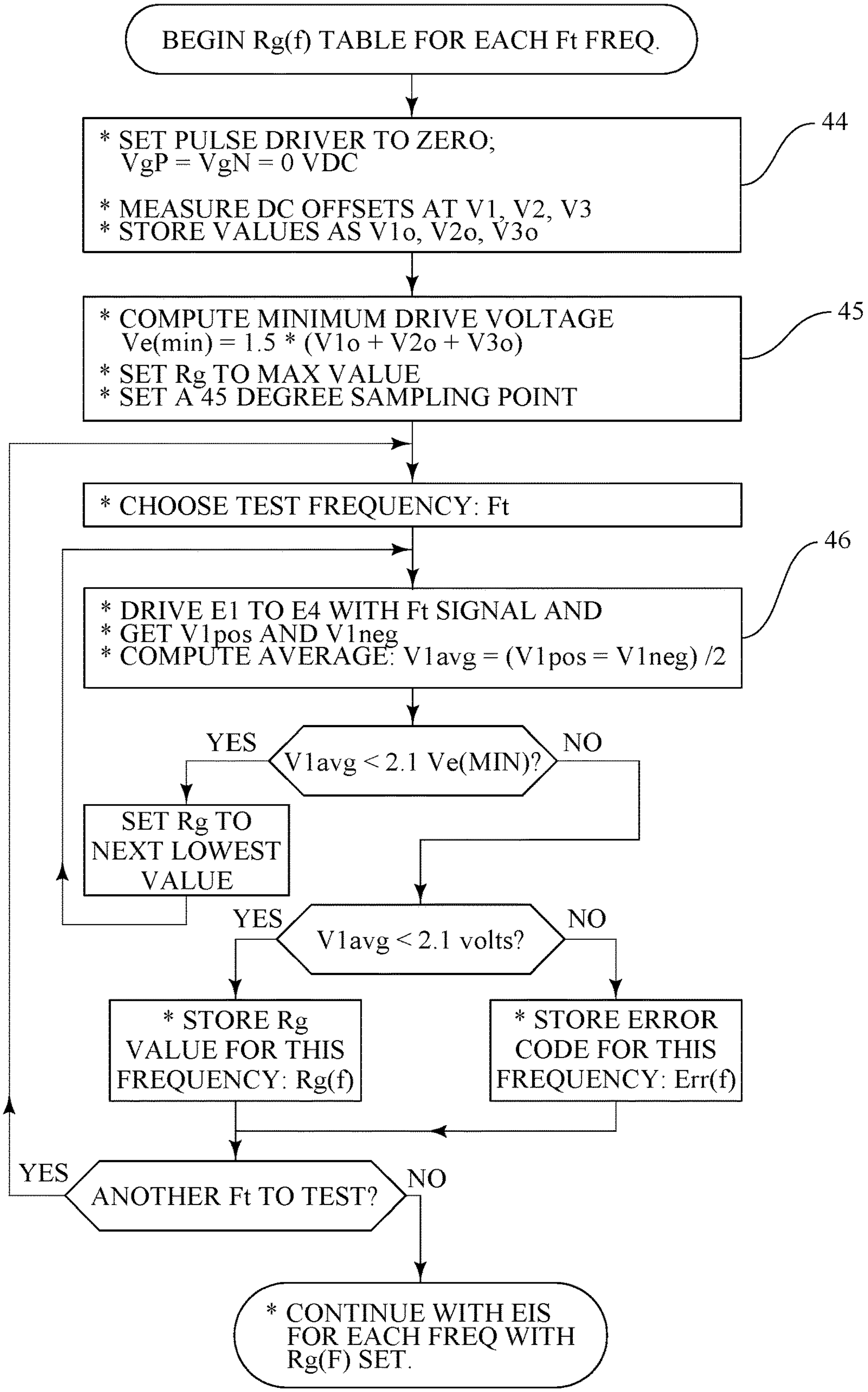
FIG. 6 is a logic flow diagram detailing a method to select a suitable pulse generator source resistance at each frequency measured.

As shown in FIG. 6, the first actions 44 in the Rg selection process are to measure the zero-drive voltage DC offsets V1o, V2o and V3o as seen at the electrodes 14, 16, 21 and 22. The next step 45 is to establish a minimum peak drive signal value across the biological load which is above the maximum expected accumulated, absolute DC offset value as determined by multiplying the sum of the zero-drive voltage DC offsets from step 45 as seen at the electrodes 14, 16, 20 and 22. In one case, the zero-drive values measured were 40 millivolts, 60 millivolts and 88 millivolts for V1o, V2o, and V3o respectively. Thus, with a 50% safety factor, a minimum electrode drive voltage, Ve(min), was computed to be (1.5×(0.04+0.06+0.088)) 0.282 volts.

The next actions 46 are to iteratively try each Rg value from the highest value toward the lowest values to find a drive potential which first causes the average sampled voltage, V1 avg, to exceed this Ve(min) value. The sampling point was chosen to be at 45 degrees (relative to the drive wave maximum amplitude) to assure approximately equal parts of real and imaginary impedance contributions. Assuming that V1 avg is less than 2.1 vdc, then that Rg value, Rg(f) is stored and used thereafter for all EIS measurements that are made at that frequency. Once Rg values are chosen for each frequency to be measured, the PKIM method then makes impedance measurements at each preselected frequency. This Rg selection process is normally only performed once but may be repeated if V1 is determined to be less than Ve(min) at any time in the future.

Figure 7:
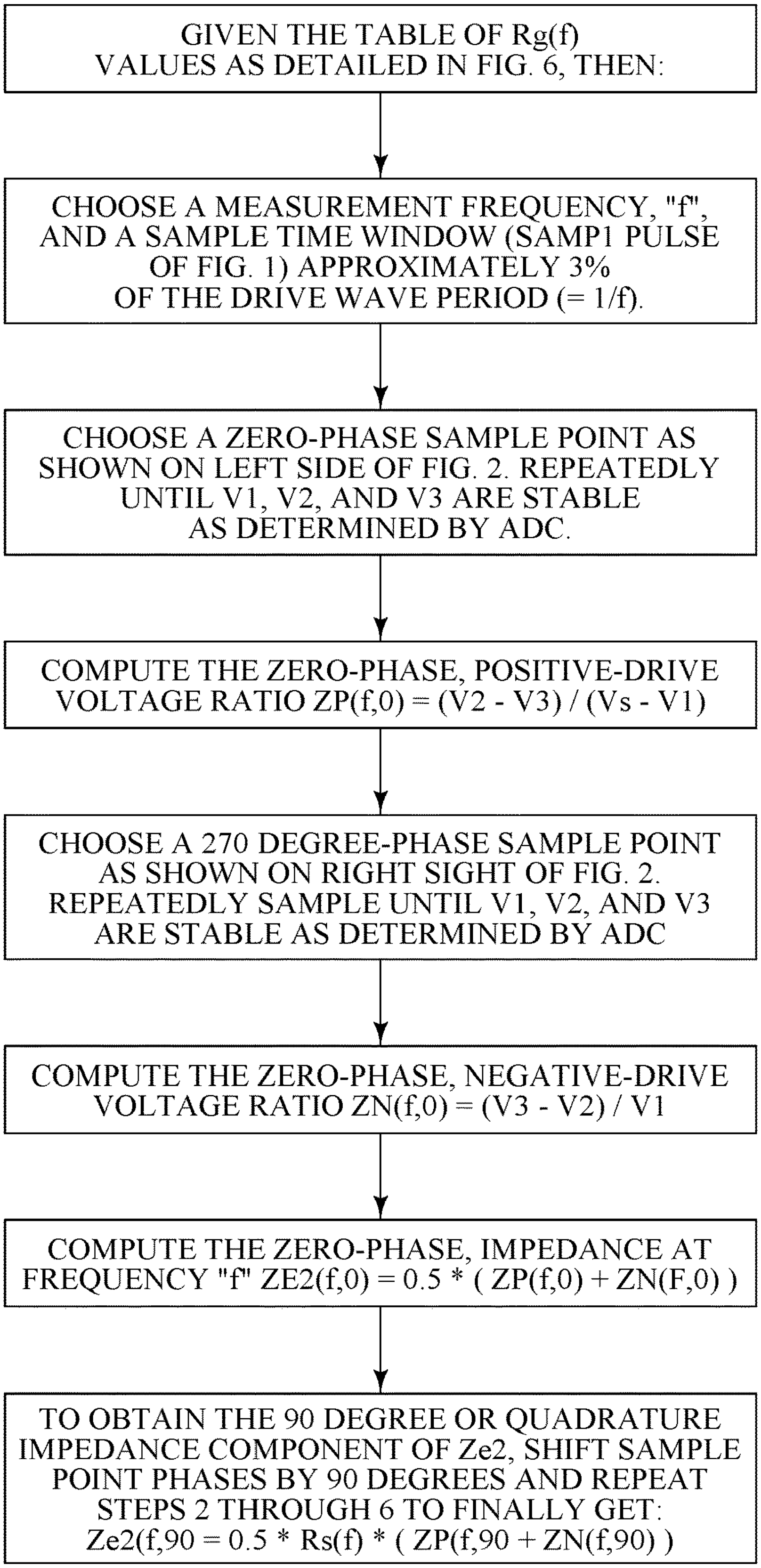
FIG. 7 is a summary of the formulae used to extract the real and imaginary impedance components of the tissue impedance.

With suitable Rg values chosen, the impedance measurement process may be started. This process is summarized in FIG. 7. The measurement frequency is selected and the Rg for that frequency as determined above and illustrated in FIG. 6 is selected. A series of phase-timed positive samples are taken on each polarity of the drive wave until V1, V2 and V3 are stable indicating that the capacitors 23 have been fully charged and the resulting ADC values of V1, V2 and V3 are saved. Polarity is reversed and The ADC values for each frequency and sample phase are uploaded by a wireless link. Then, post processing in a more competent computer is performed. However, FIG. 7 shows the overall computations performed. Note that by taking the average of the ZP and ZN impedances that the electrode DC bias voltages (Vb #) are cancelled out. Thus, AC coupling capacitors are not required.

Figure 8:
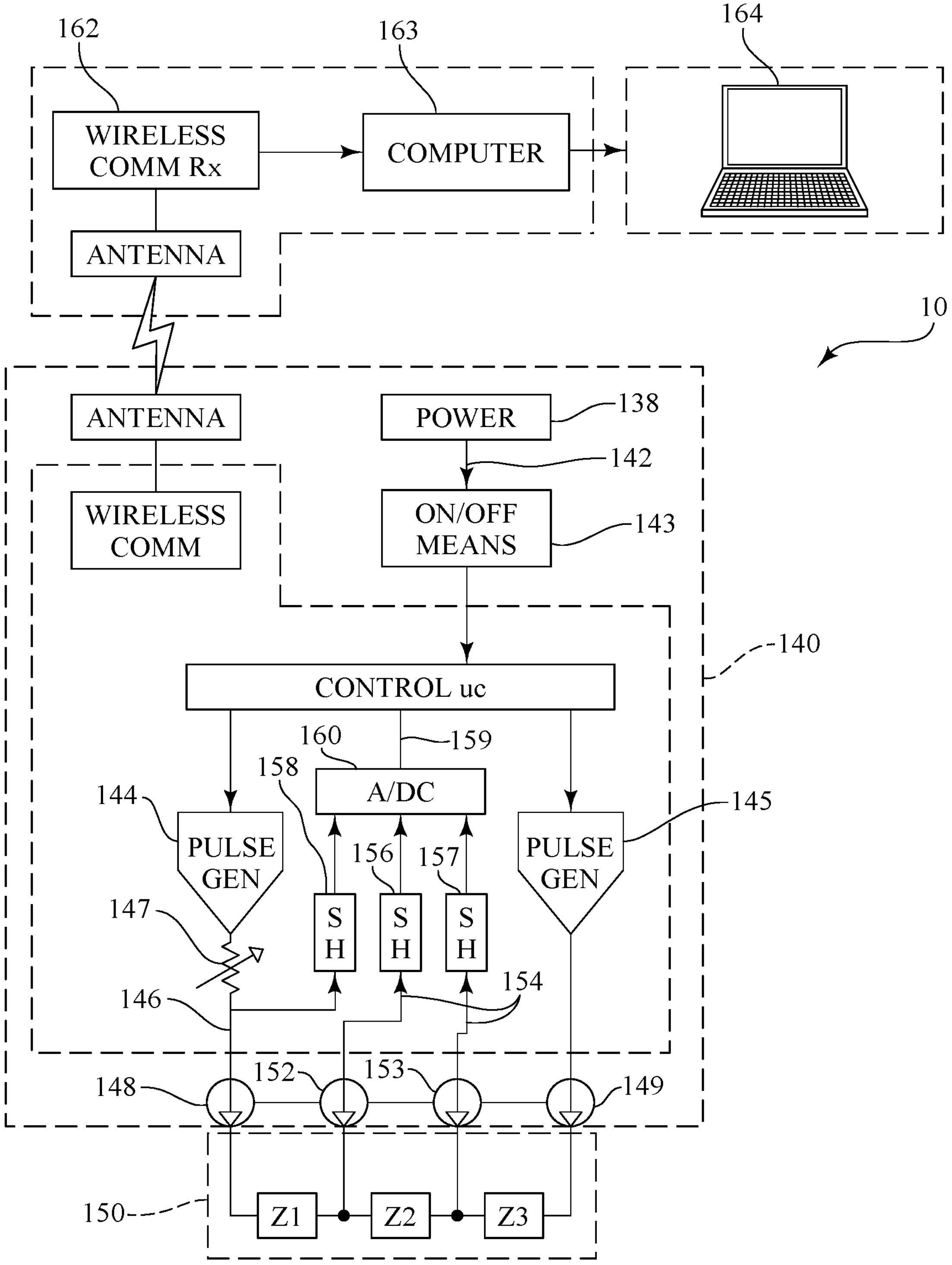
FIG. 8 is a functional block diagram of a preferred embodiment of the invention.

Referring to FIG. 8 a block diagram of one embodiment of the circuitry of the invention that can be miniaturized for use in a micro-device is illustrated. In this embodiment power 138 is direct current supplied by a 3V battery to a micro-controller 140 through line 142. An on/off switch 143 for activating the device is in line 142. The micro-controller 140 is provided with two pulse generators, 144 for positive pulse and 145 for negative pulses. A line 146 connects the pulse generator 144 with an injection electrode 148 for injecting positive current pulses into a biological load 150 in which Z1, Z2 and Z3 represent tissue impedance. For positive current pulses electrode 149 is at common. A variable resister 147 is in the line 146 for controlling current. An electrode 149 is provided for injection of negative current pulses. The potential of each current pulse is sensed by electrodes 152 and 153 and the sensed charge is passed through lines 154 to sample and hold capacitors 156 and 157. The sample and hold capacitor 158 is for determination of the potential of the input current pulses before reaching the biological load 150. A positive and negative pulse is generated during each cycle and for measuring the positive potential the sine wave sampling point is preferably about 90° until maximum positive potential is built up at the sample and hold capacitors 156 and 157. The circuit polarity and sampling point is then changed by the micro-controller 140 to about 270° until maximum negative potential is built up at the sample and hold capacitors 156 and 157. Sampling current pulses after maximum potential is stored by the sample and hold capacitors 156 and 157 increments of the pulses have no further effect on the stored charge indicating that the maximum potential of the biological load has been reached. This maximum potential is routed through line 159 to an analog to digital converter 160 for digitization and the digitized potential is stored in the random-access memory of the micro-controller 140.

The digitized potential is wirelessly transmitted to an external receiver 162. The external receiver 162 may be a nearby computer for computation to impedance and subsequent display of the computed impedance or a computer or other device, such as a cell phone, which includes a more robust transmission system for relaying the digitized potential to a remote computer 164 for computing the impedance and displaying the computed impedance.

EXAMPLE

Lymphedema is a chronic disease that produces swelling in body tissue due to fluids caused by a malfunction of the lymphatic system. Breast cancer patients who have had some or all the lymph nodes removed from an arm due to the progress of the cancer are subject to contracting lymphedema. Early detection and treatment can reduce the severity of the disease although in its very early stages (subclinical lymphedema), but it is extremely difficult to detect by conventional clinical methods, such as measurement of the dimensions of the arm, to detect swelling in the case of breast cancer patients. Subclinical lymphedema normally progresses into chronic lymphedema. Subclinical lymphedema can exist in the body with no outward or detectable sign for months.

Bioimpedance as a screening tool for lymphedema is under study, particularly as it is non-invasive and is relatively inexpensive. The impedance of the tissue is affected by the buildup of fluid. The PKIM circuitry of the present invention is highly suited for screening purposes as it simulates electro impedance spectroscopy (EIS) in its operation, and it can be miniaturized for convenient wear by the patient.

Figure 9:
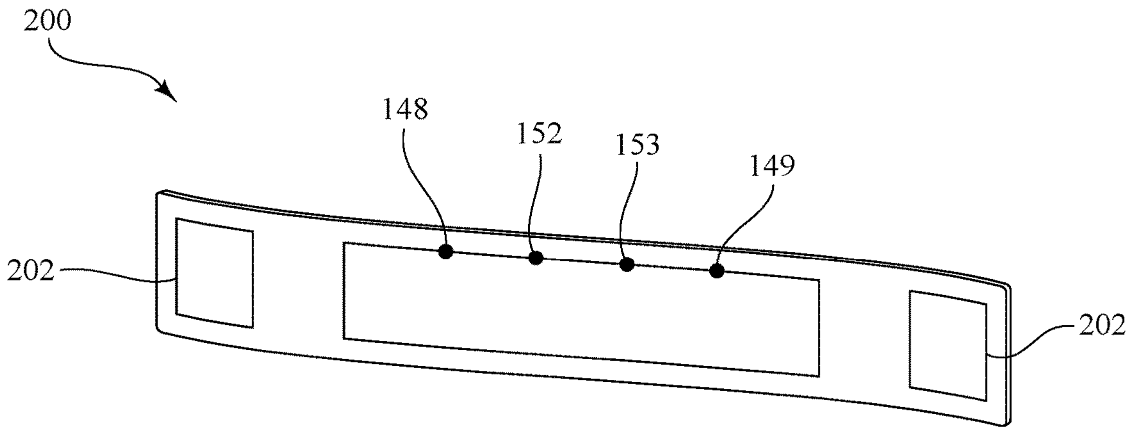
FIG. 9 illustrates a physical overview of one embodiment of the invention.
Figure 10:
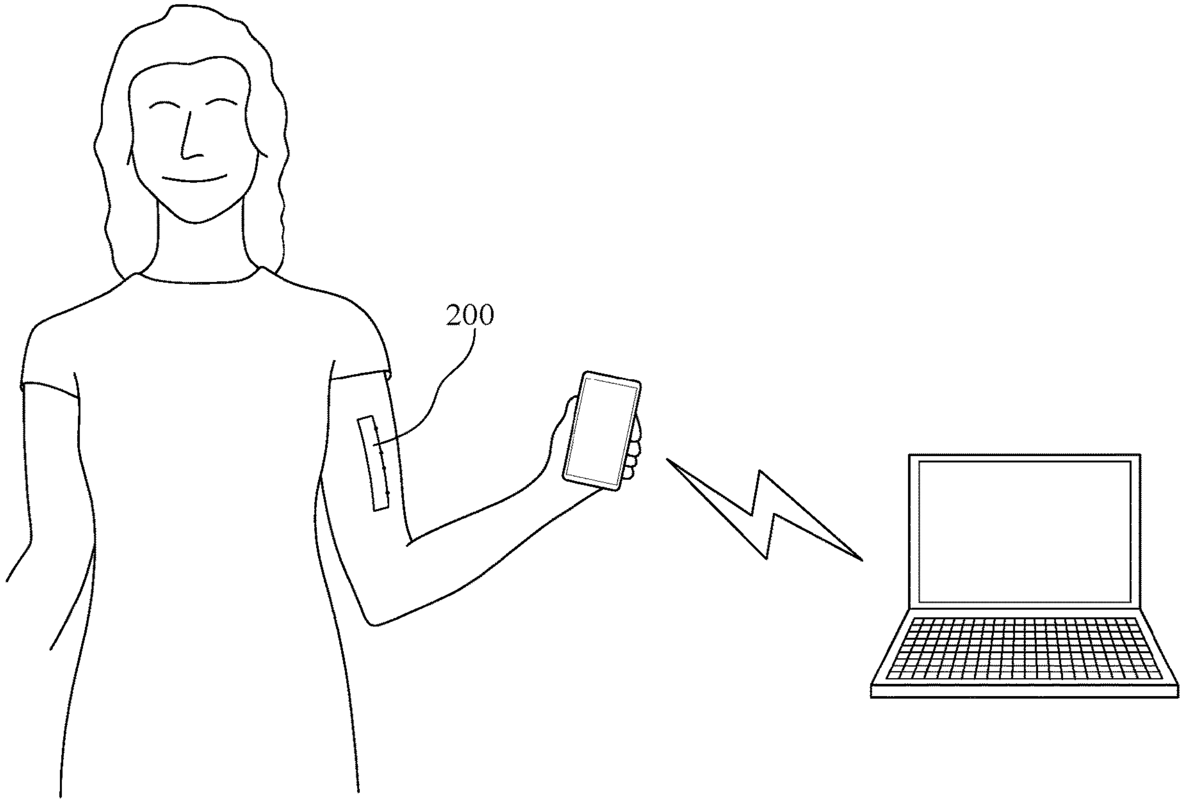
FIG. 10 illustrates one application of the embodiment of FIG. 9.

Referring to FIGS. 9 and 10 where like numbers denote like components and like functions, a micro-device 200 (FIG. 9) in the form of an adhesive strip 10 approximately the size of a includes the circuit of FIG. 8 is affixed to the patient by a strip 200 of surgical tape approximately the size of an adhesive bandage used for minor wounds. As an alternative embodiment, the micro-device 200 may form part of an elastomeric or adjustable band that can be conveniently worn on the patient's arm or leg. An adhesive 202 may applied to at least at both ends of the strip 200 to further secure the strip to the area of the patient's body being scanned. It will be understood that the micro-device 200 may be of any suitable shape and size that can be conveniently worn by a mobile patient. Electrodes 148, 149, 152 and 153 are exposed for contact with the patient's skin. In the case of a breast cancer patient the strip 200 or at least the electrodes 148, 149, 152 and 153 will be placed on the underside of the patient's arm. A series of positive pulses followed by a series of negative pulses are charged into the tissue of the arm and the resulting positive potential and negative potential are digitized, averaged and wirelessly transmitted to the external receiver 162 for computation of tissue impedance. Normally, the external receiver 162 is a cell phone or preferably, a small conventional receiver/transmitter which can be worn by the patient, and which automatically transmits the digitized potential to computer for computation of impedance. Good practice will have a strip 200 worn on an unaffected part of the patient's body for reference impedance measurements. It will be understood that the strip 200 can be readily moved to other parts of the patient's body such as the leg where lymphedema often occurs.

It will be understood that the micro-device presents a non-invasive and painless method for early detection of lymphedema and is utilized in a form that can be worn for an extended period. Persons at risk for lymphedema, such as breast cancer patients, may be screened immediately after surgery and for a period of time thereafter so that tissue swelling due to fluids may be recognized early on and treatment can be started to reduce the effects of lymphedema.

The present invention allows for the advantages of electro impedance spectroscopy to be achieved by a micro-device powered by a low voltage direct current battery. The parts count of the micro-device is reduced allowing for substantial miniaturization.

The embodiments disclosed above are illustrative only, as the disclosure may be modified and practiced in different but equivalent manners apparent to those skilled in the art having the benefit of the teachings herein. Furthermore, no limitations are intended to the details of construction or design herein shown, other than as described in the claims below. The embodiments disclosed above may be altered or modified and all such variations are considered within the scope and spirit of the disclosure. Accordingly, the protection sought herein is as set forth in the claims below.

I claim:

1. A method for simulating alternating current and determining tissue impedance of a biological load comprising:

a. driving a series of timed, low-power, direct current pulses of known frequency, amplitude, and driver resistance into a biological load, the series of timed low-power, direct current pulses approximate sinusoidal driven pulses by selection of drive frequencies in which pulse harmonics encounter the same impedance as a fundamental frequency, wherein the low-power direct current for the series of low-power, direct current pulses is selected so that voltages of the timed, low-power, direct current pulses of known frequency, amplitude, and driver resistance are large enough to overcome an accumulated DC bias offset electrode voltages but not so large as to cause electrolysis to occur, b. sampling an increment of potential through the biological load of each of the low-power, direct current pulses of known frequency, amplitude, and driver resistance of the series, and accumulating each increment of potential until accumulated maximum potential through the biological load is reached, c. converting the accumulated maximum potential to a digital format and calculating tissue impedance of the biological load.

2. The method of claim 1, wherein resistance of each of timed, low-power, direct current pulses of the series of known frequency, amplitude, and driver resistance is selected between 1.0K and 10K.

3. The method of claim 1, wherein power for the series of timed, low-power, direct current pulses of known frequency, amplitude, and driver resistance is supplied by a 3-volt battery.

4. The method of claim 1, wherein each of the timed, low-power, direct current pulses of the series is sampled at an identical point of each waveform of the timed, low-power, direct current pulses of the series to reduce odd harmonics.

5. The method of claim 1, wherein non-zero potentials of the pulses of each of timed, low-power, direct current pulses of known frequency, amplitude and driver resistance of the series are sampled at between 66° and 135° of a total pulse time wave cycle.

6. The method of claim 1, wherein the sinusoidal-driven, timed, low-power, direct current pulses of known frequency, amplitude, and driver resistance are approximated by selection of drive frequencies for each pulse in which pulse harmonics encounter the same impedance as the fundamental frequency.

7. The method of claim 1, wherein an amplitude of timed, low-power, direct current pulses of known frequency, amplitude, and driver resistance of the series is less than 2.1 volts.

8. The method of claim 1, wherein, a first series of positively driven timed, low-power, direct current pulses of known frequency, amplitude, and driver resistance is driven into the biological load when a supply current is drawn from a known power supply voltage, sampling the increment of potential of each positively driven timed, low-power, direct current pulse of known frequency, amplitude, and driver resistance and accumulating each increment of potential until the maximum potential of the first series of positively driven pulses through the biological load is reached, converting the reached potential of the first series of pulses to digital format and calculating positive impedance, and a second series of negatively driven timed, low-power, direct current pulses of known frequency, amplitude, and driver resistance is driven into the biological load when the supply current is drawn from a local common, and sampling an increment of potential of each negatively driven timed, low-power, direct current pulse of known frequency, amplitude, and driver resistance, and accumulating each increment of potential of each negatively driven pulse of timed, low-power, direct current pulse of known frequency, amplitude, and driver resistance through the biological load until maximum potential of the second series of negatively driven timed, low-power, direct current pulses of known frequency, amplitude, and driver resistance through the biological load is reached, and converting the reached potential to digital format and calculating negative impedance, and taking an average of potential of the first series of positively driven pulses and the second series of negatively driven pulses to determine an unbiased impedance value.

9. The method of claim 8, wherein each pulse of the positively driven and negatively driven series of the timed, low-power, direct current pulses of known frequency, amplitude, and driver resistance is sampled for potential at a selected point on the pulse waveform, wherein frequency of the first series and second series of pulses is determined by selection of drive frequencies in which pulse harmonics encounter-the same impedance as the fundamental frequency and wherein the low power direct current is selected so that voltages of timed, low-power, direct current pulses of known frequency, amplitude, and driver resistance are large enough to overcome accumulated DC bias offset electrode voltages but not so large as to cause electrolysis to occur.

* * * * *